United States Patent [19]
Webb, Jr. et al.

[11] Patent Number: 5,167,957
[45] Date of Patent: Dec. 1, 1992

[54] COMPOSITIONS AND METHODS FOR THE TREATMENT OF DIETARY DEFICIENCIES

[75] Inventors: Kenneth E. Webb, Jr.; Douglas B. DiRienzo, both of Blacksburg, Va.

[73] Assignee: Virginia Tech Intellectual Properties, Inc., Blacksburg, Va.

[21] Appl. No.: 578,186

[22] Filed: Sep. 6, 1990

[51] Int. Cl.$^5$ ..................... A61K 35/00; A61K 37/00
[52] U.S. Cl. ...................................... 424/115; 514/2
[58] Field of Search ................. 514/2, 400, 419, 423, 514/561, 562, 564, 565, 566; 424/115

[56]  References Cited
U.S. PATENT DOCUMENTS

| | | | |
|---|---|---|---|
| 3,697,287 | 10/1972 | Winitz | 514/561 |
| 4,340,592 | 7/1982 | Adibi | 514/561 |
| 4,595,584 | 6/1986 | Wu et al. | 424/438 |

FOREIGN PATENT DOCUMENTS 0182356 5/1986 European Pat. Off. .

OTHER PUBLICATIONS

Evidence for active transport of the dipeptide glycylsarcosine by hamster jejunum in vitro. Addison, et al., Clin. Sci. 43:907–911 (1972).
A Common Mechanism For Transport of Di-and Tri--peptides by Hamster Jejunum In Vitro., Addison et al., Clin. Sci. Mol. Med. 49:313–322 (1975).
Competition Between Carnosine and Other Peptides For Transport by Hamster Jejunum In Vitro., Addison et al., Clin. Sci. Mol. Med. 46:707–714 (1974).
Evidence for Active Transport of Tripeptides by Hamster Jejunum In Vitro., Addison et al., Clin. Sci. Mol. Med., 49:305–312 (1974).
Intestinal Transport of Dipeptides in Man: Relative Importance of Hydrolysis and Intact Absorption., Adibi, J. Clin. Invest. 50:2266–2275 (1971).
Intestinal Phase of Protein Assimilation in Man. Adibi, Am. J. Clin. Nutr. 29:205–215 (1976).
Amino Acid and Peptide Absorption in Human Intestine: Implications for Enteral Nutrition., Adibi, Amino Acids, Metabolism and Medical Applications, pp. 255–263 (1983).
Functional Characterization of Depeptide Transport System in Human Jejunum., Adibi et al., J. Clin. Invest. 53:1368–1374 (1974).
Peptide Absorption and Hydrolysis., Adibi, et al., Physiology of the Gastrointestinal Tract, pp. 1073–1095 (1981).
Evidence for Two Different Modes of Tripeptide Disappearance in Human Intestine., Adibi, et al., J. Clin. Invest., 56:1355–1363 (1975).
Influence of Molecular Structure on Half-Life and Hydrolysis of Dipeptides in Plasma: Importance of Glycine as N-terminal Amino Acid Residue., Adibi et al., Metab. 35:830–836 (1986).
Comparison of Free Amino Acid and Dipeptide Absorption in the Jejunum of Sprue Patients., Adibi et al., Gastroenterology 67:586–591 (1974).
Availability of Amino Acids Supplied Intravenously in Healthy Man as Synthetic Dipeptides: Kinetic Evaluation of L-alanly-L-glutamine and glycyl-L-tyrosine. Albers et al., Clin. Sci., 75:463–468 (1988).

(List continued on next page.)

Primary Examiner—Frederick E. Waddell
Assistant Examiner—Raymond J. Henley, III
Attorney, Agent, or Firm—Mason, Fenwick & Lawrence

[57]  ABSTRACT

Compositions containing peptides which are capable of absorption in the stomach are supplied to animals, such as but not limited to ruminants, in order to supply nutrients and treat dietary deficiencies. In a preferred embodiment, peptides containing at least one other amino acid which animals are deficient in are supplied to animals to treat specific amino acids deficiencies. Preferably, the peptides contain glycine, phenylalanine, or proline, and the peptides are formed from a total of four or less amino acid residues. An alternative embodiment involves formulation of peptide derivatives through the attachment of mineral compounds or medicaments to peptides, and the peptide derivatives are then supplied to the diet to treat mineral deficiencies or illnesses. The compositions and methods are particularly useful in treating amino acid deficiencies, such as but not limited to methionine deficiencies in ruminants.

12 Claims, 2 Drawing Sheets

OTHER PUBLICATIONS

Availability of Amino Acids Supplied by Constant Intravenous Infusion of Synthetic Dipeptides in Healthy Man., Albers et al., *Clin. Sci.*, 76:643–648 (1989).

Digestion and Absorption of Carbohydrates and Proteins. Alpers, *Physiology of the Gastrointestinal Tract* (2nd Ed.) pp. 1469–1487 (1987).

Metabolism of Amino Acids by Rate Stomach In Vivo. Anderson, et al., *Biochem. Soc. Trans.*, 11:297–298 (1983).

Nitrogen Metabolism in the Sheep., Annison, *Biochem. J.*, 64:705–714 (1956).

Digestion of Nitrogenous Substances Entering the Small Intestine with Particular Reference to Amino Acids in Ruminant Livestock., Armstrong et al., *Proceedings of the 2nd Symposium on Protein Metabolism and Nutrition*, May 2–6, 1977, pp. 55–60.

Intestinal Absorption of Stereoisomers of Dipeptides in the Rat., Asatoor, et al., *Clin. Sci. Mol. Med.* 45:199–212 (1970).

Intestinal Absorption of Oligopeptides in Cystinuria., Asatoor et al., *Clin. Sci.* 41:23–33 (1971).

Delta Sleep-inducing Peptides (DSIP)–like Material is Absorbed by the Gastrointestinal Tract of the Neonatal Rat., Banks, et al., *Life Sci.* 33:1587–1597 (1983).

Animal Nutrition., Bondi, New York, pp. 153–167 (1987).

Intestinal Absorption of Dipeptides Containing Glycine, Phenylalanine, Proline, Beta-alanine or Histidine in the Rat., Boullin, et al., *Clin. Sci. Mol. Med.* 45:849–858 (1973).

Effects of Dietary Nitrogen Source on Concentrations of Ammonia, Free Amino Acids and Fluorescamine-Reactive Peptides in the Sheep Rumen., Broderick, et al., *J. Anim. Sci.* 66:2233-2 (1988).

Metabolism of Peptides and Amino Acids During In Vitro Protein Degradation by Mixed Rumen Organisms, Broderick et al., *J. Dairy Sci.* 72:2540–2548 (1989).

Effects of Sodium Replacement on Uptake of the Dipeptide Glycylsarcosine by Hamster Jejunum In Vitro, Burston, et al., *Clin. Sci.* 73:61–68 (1987).

Intestinal Handling of Two Tetrapeptides by Rodent Small Intestine In Vitro, Burston et al., *Biochem. Biosphys., Acta* 553:175–178 (1979).

Uptake of Dipeptides Containing Basic and Acidic Amino Acids by Rat Small Intestine In Vitro, Burston et al., *Clin. Sci.* 43:823–837 (1972).

Uptake of L-valyl-L-valine and Glycylsarcosine by Hamster Jejunum In Vitro., Burston et al., *Clin. Sci.* 62:617–626 (1982).

Efficiency of Utilization of Absorbed Amino Acids for Growth., Buttery, Proceedings from the AFIA Nutrition Symposium, Nov. 12–13, 1986, St. Louis, MO.

Ionic Dependence of Glycylsarcosine Uptake by Isolated Chicken Enterocytes., Calonge et al., *J. Cell. Phys.* 138:579–585 (1989).

Glycylsarcosine Transport by Epithelial Cells Isolated from Chicken Proximal Cecum and Rectum., Calonge et al., *Am. J. Physiol.*, 258:G660–G664 (1990).

The Effect of Amino Acids and Dipeptides on Sodium-ion Transport in Rat Enterocytes., Cheeseman et al., *Biochem. Biophys.* Acta 812:767–773 (1985).

Specific Transfer Process for Intestinal Absorption of Peptides., Cheesman et al., *Physiol.* 229:45P–46P (1972).

Interaction of Amino Acids, Peptides and Peptidases in the Small Intestine., Cheeseman et al., *Proc. R. Soc. Lond.* 190:149–163 (1975).

The Role of Some Small Peptides in the Transfer of Amino Nitrogen Across the Wall of Vascularly Perfused Intestine., Cheeseman et al., *J. Physiol.*, 262:459–476 (1976).

Concentration and Estimated Flow of Peptides from the Rumen of Dairy Cattle: Effects of Protein, Quality, Protein Solubility, and Feeding Frequency., Chen. et al. *J. Dairy Sci.* 70:983–992 (1987).

Effect of Hydrophobicity on Utilization of Peptides by Ruminal Bacterial In Vitro., Chen et al., *Appl. Environ. Microbiol.*, 53:2021–2025 (1987).

A Procedure for Measuring Peptides in Rumin Fluid and Evidence that Peptide Uptake can be a Rate-limiting Step in Ruminal Protein Degradation., Chen et al., *J. Dairy Sci.* 70:1211–1219 (1987).

Mechanisms of Dipeptide Uptake by Rat Small Intestine In Vitro., Cheng et al. *Clin. Sci.* 40:247–259 (1971).

Conjugated Amino Acids in Portal Plasma of Dogs After Protein Feeding., Christensen, *Biochem. J.* 44:333–335 (1949).

Digestive Physiology and Nutrition of Ruminants. Church, vol. 1–*Digestive Physiology* (2nd Ed.) pp. 227–252 (1975).

(List continued on next page.)

OTHER PUBLICATIONS

Amino Acid and Peptide Absorption in Patients with Coeliac Disease, Clark et al., *The Use of Amino Acids and Oligopeptides in Dietetics*, pp. 32–37 (1977).

Protein Metabolism in the Rumen. I. Absorption of Glycine and Other Amino Acids., Cook et al., *J. Dairy Sci.* 48:475–483 (1965).

Degradation and Outflow of Amino Acids from the Rumen of Sheep., Cottle et al., *Br. J. Nutr.* 61:397–408 (1989).

Sites of Maximal Absorption and Hydrolysis of Two Dipeptides by Rat Small Intestine in Vivo., Crampton et al., *Clin. Sci.* 44:583–594 (1973).

Rates of Absorption by Rat Intestine of Pancreatic Hydrolysates of Proteins and Their Corresponding Amino Acid Mixtures, Crampton et al., *Clin. Sci.* 41:409–417 (1971).

Studies on a Wide-spectrum Intestinal Dipeptide Uptake System in the Monkey and in the Human, Das et al., *Biochem. J.* 146:133–139 (1975).

An investigation into Protein Digestion with 14C-labelled Protein 2. The Transport of 14C-labelled Nitrogenous Compounds in the Rat and Cat., Dawson et al. *Brit J. Nutr.* 16:27–38 (1962).

Studies on the Absorption of Proteins: The Amino Acid Pattern in the Portal Blood., Dent et al., *Biochem. J.* 44:318–332 (1949).

Dietary Regulation of Intestinal Transport of the Dipeptide Carnosine., Ferraris et al., *Am. J. Physiol.* 255:G143–G150 (1988).

Assessment of the Role of Brush-border Peptide Hydrolases in the Luminal Disappearance of Dipeptides In Man., Fogel et al, *J. Lab. Clin. Med.* 84:327–333 (1974).

Role of pH Gradient and Membrance Potential in Dipeptide Transport in Intestinal Renal Brush-border Membrane Visicles from the Rabbit., Ganapathy et al., *J. Bio. Chem.* 258:14189–14192 (1983).

Is Intestinal Peptide Transport Energized by a Proton Gradient?, Ganapathy et al., *Am. J. Phys.* 249:G153–G160 (1985).

Absorption of Amino Acids and Peptides from a Complex Mixture in the Isolated Small Intestine of the Rat. Gardner, *J. Physiol.* 253:233–256 (1975).

Amino Acid and Peptide Absorption from Partial Digests of Proteins in Isolated Rat Small Intestine., Gardner, *J. Physiol.* 284:83–104 (1978).

Superficial or Membrane Digestion of Peptides in Dinitrophenol-inhibited Rat Small Intestine. Gardner, *Clin. Sci.* 57:217–220 (1979).

Absorption of Intact Peptides: Studies on Transport of Protein Digests and Dipeptides Across Rat Small Intestine In Vitro., Gardner, *Quart. J. Exp. Physiol.* 67:629–637 (1982).

Evidence for, and Implications of, Passage of Intact Peptides Across the Intestinal Mucosa, Gardner, *Biochem. Soc. Trans.* 11:810–813 (1983).

Intestinal Assimilation of Intact Peptides and Proteins from the Diet-A Neglected Field? Gardner, *Bio. Rev.* 59:289–331 (1984).

Trans-mucosal Passage of Intact Peptides in the Guinea-pig Small Intestine In Vivo: A Re-appraisal. Gardner, et al., *Clin. Sci.* 64:433–439 (1983).

Amino Acid and Peptide Absorption After Proximal Small Intestinal Resection in the Rat., Garrido, Jr., et al., *Gut* 20:114–120 (1979).

Peptides in Human Nutrition., Grimble, et al., *Nutr. Res. Rev.* 2:87–108 (1989).

Portal-drained Visceral Flux of Nutrients in Lambs Fed Alfalfa or Maintained by Total Intragastric Infusion. Gross, et al., *J. Anim. Sci.* 68:214–221 (1990).

Portal Absorption of Small Peptides in Rats Under Unrestrained Conditions., Hara, et al., *J. Nutr.* 114:1122–1129 (1984).

Apsorption of Two Tyrosine Containing Tripeptides from the Small Intestine and Rectum of the Rat. Heading, et al., *J. Pharm. Pharmacol.* 31:39P (1979).

Intestinal Absorption of Glycyl-L-proline in the Rat. Heading, et al., *Clin. Sci. Mol. Med.* 52:607–614 (1977).

Intestinal Dipeptide Transport in Normal and Cystinuric Subjects., Hellier, et al., *Clin. Sci.* 43:659–668 (1972).

Quantitative Studies on Amino Acid Absorption in Sheep. Hume, et al., *J. Nutr.* 102:495–506 (1972).

The Rumen and Its Microbes., Hungate, Academic Press, New York (1966).

Net Absorption and Oxygen Consumption by Holstein Steers Fed Alfalfa or Orchardgrass Silage at Two Equalized Intakes., Huntington, et al., *J. Anim. Sci.* 66:1292–1302 (1988).

Digestion of Protein in the Intestine of Adult Ruminants. Kay, *Symp. Proc.* 28:140–151 (1969).

The Absorption of Amino Acids from the Rumen of the Sheep. I. The Loss of Amino Acids from Solutions Placed in the Washed Rumen In Vivo., Leibholz, *Aust. J. Agric. Res.* 22:639–645 (1971).

(List continued on next page.)

OTHER PUBLICATIONS

The Absorption of Amino Acids from the Rumen of the Sheep. II. The Transfer of Histidine, Glycine and Ammonia Across the Rumen Epithelium in Vitro., Leibholz, *Aust. J. Agric. Res.*, 22:647–653 (1971).

Nature and Appearance of Protein Digestion Products in Upper-mesenteric Blood., Levenson, et al., *Proc. Soc. Exp. Biol. Med.* 101:178–180 (1959).

Metabolism of Amino Acids in the Bovine Rumen. Lewis, et al., *J. Dairy Sci.* 45:1487–1492 (1962).

Absorption of Di- and Tripeptides by the Intestine of the Guinea-pig, Lindblad, et al., *Ciba Foundation Symposium* 70, pp. 189–200, Excerpta Medica, NY (1979).

Effects of Dietary Restriction and Protein Deprivation of Intestinal Absorption of Protein Digestion Products in the Rat., Lis, et al., *Br. J. Nutr.* 28:443–446 (1972).

Rates of Absorption of a Dipeptide and the Equivalent Free Amino Acid in Various Mammalian Species, Lis et al., *Biochim. Biophys.*, Acta 233:453–455 (1971).

Effect of Dietary Changes on Intestinal Absorption of L-methionine and L—methionine in the Rat, Lis et al., *Br. J. Nutr.* 27:159–167 (1972).

Metabolism of Dipeptides and Their Constituent Amino Acids by Liver, Gut, Kidney and Muscle, Lochs et al., *Am. J. Physiol.*, 254:E588-E-594 (1988).

Intestinal Absorption of Peptides, Matthews, *Physiol. Rev.* 55:337–608 (1975).

Memorial Lecture: Protein Absorption-Then and Now, Matthews, *Gastroenterology* 73:1267–1279 (1977).

Intestinal Absorption of Peptides, Matthews, *Biochem. Soc. Trans.* 11:808–810 (1983).

Progress in Gastroenterology-Peptide Absorption, Matthews, et al. *Gastroenterology* 71:151–161 (1976).

Absorption of Glycine and Clycine Peptides from the Small Intestine of the Rat, Matthews, et al., *Clin. Sci.* 35:415–424 (1968).

Evidence for Active Transport of the Dipeptide Carnosine (beta-alanyl-L-his-tidine) by Hamster Jejunum In Vitro, Matthews, et al., *Clin. Sci. Mol. Med.* 46:693-7-05 (1979).

Influx of Two Dipeptides, Glycylsarcosine and L--glutamyl-L-glutamic Acid, into Hamster Jejunum In Vitro, Matthews, et al., *Clin. Sci,* 56:15–23 (1979).

Animial Nutrition, Maynard, et al., McGraw-Hill Book Co., New York, pp. 158–167 (1979).

Animal Nutrition (2nd Ed.), McDonald et al., Longman, Inc., New York, pp. 134–146 (1978).

Ruminant Nitrogen Usage, NRC, National Academy Press, Washington, D.C. (1985).

Protein Nutrition in Ruminants, Orskov, Academic Press, New York (1982).

Protein Utilization in Ruminants: Current Concepts In Formulating Ruminant Diets, Owens, *AFIA Nutrition Symposium* (Nov. 12–13, 1986) St. Louis, MO.

The Absorption of Flycine and Glycine Oligopeptides by the Rat, Peters, et al., *Clin. Sci.* 39:811–821 (1970).

Peptides and Other Nitrogen Sources for Growth of Bacteriodes Ruminicola, Pittman, et al., *J. Bact.* 88:401–410 (1964).

Oligopeptide Uptake by Bacteriodes Ruminicola, Pittman, et al., *J. Bact.* 93:1499–1508 (1967).

Influence of Diet on Amino Acid Absorption in Beef Cattle and Sheep, Prior et al., *J. Nutr.* 111:2212–2222 (1981).

Net Portal-drained Viscera and Hepatic Metabolism of Glucose, L-lactate and Nitrogenous Compounds in Lactating Holstein Cows, Reynolds et al., *J. Dairy Sci.* 71:1803–1812 (1988).

Intestinal Transport of Amino Acid Residues of Dipeptides.—Influx of the Glycine Residue of Flycyl-L-proline Across Mucosal Border, Rubino, et al., *J. Bio. Chem.* 246:3542–3548.

Hydrolysis and Absorption of Proline Dipeptides Across the Wall of Sacs Prepared from Everted Rat Intestine, Saidel, *Biochim. Biophys. Acta* 367:75–80 (1974).

Diglycine Absorption in Streptozotocin Diabetic Rat, Schedl, et al., *Am. J. Physiol* 235:E457–E460 (1978).

Kinetics of Uptake of an Amino Acid and a Dipeptide into Hamster Jejunum and Ileum: The Effect of Semistarvation and Starvation, Schedl, et al., *Clin. Sci.* 56:487–492 (1979).

Dipeptide Transport in Isolated Intestinal Brush Border Membrane, Sigrist-Nelson, *Biochim. Biophys.* 394:220–226 (1975).

Absorption of Amino Acids and Peptide Meals in Normal Human Subjects, Silk, *The Use of Amino Acids and Oligopeptides in Dietics*, pp. 24–31 (1977).

Peptide Transport, Silk, *Clin. Sci.* 60:607–615 (1981).

Intestinal Transport of Two Dipeptides Containing the Same Two Neutral Amino Acids in Man, Silk, *Clin. Sci. Mol. Med.* 45:291–299 (1973).

Jejunal and Ileal Absorption of Dibasic Amino Acids and an Arginine-containing Depeptide in Cystinuria, Silk, *Gastroenterology* 68:1426–1432 (1975).

(List continued on next page.)

OTHER PUBLICATIONS

Protein Digestion and Amino Acid and Peptide Absorption, Silk, *Proc. Nutr. Soc.* 44:63-72 (1985).

Jejunal Absorption of an Amino Acid Mixture Simulating Casein and an Enzymic Hydrolysate of Casein Prepared for Oral Administration to Normal Adults, Silk, *Br. J. Nutr.* 33:95-100 (1975).

Absorption of Amion Acids From an Amino Acid Mixture Simulating Casein and a Tryptic Hyrdolysate of Casein in Man, Silk, et al, *Clin. Sci. Mol. Med.* 45:715-719 (1973).

Comparison of Oral Feeding of Peptide and Amino Acid Means to Normal Human Subjects, Silk, *Gut* 20:291-299 (1979).

Evidence for a Single Common Carrier for Uptake of a Dipeptide and a Tripeptide by Hamster Jejunum In Vitro, Sleisenger et al, *Gastroenterology* 71:76-81 (1976).

Amino Acid Concentrations in Portal Venous Plasma During Absorption from the Small Intestine of the Guinea Pig of an Amino Acid Mixture Simulating Casein and a Small Partial Enzymic Hydrolysate of Casein, Sleisinger et al., *Clin. Sci. Mol. Med.* 52:259-267 (1977).

Amino Acid and Peptide Transport Across the Mammalian Small Intestine, Smith et al., *Protein Metabolism and Nutrition*, Proc. IVth Int. Symp (9/5-9/83) pp. 211-232.

Net Amino Acid Absorption in Steers Fed Alfalfa Hay Cut at Two Stages of Maturity, Sniffen et al., *J. Dairy Sci.* 58:371-385 (1975).

In Vivo Utilization of Cystine-containing Synthetic Short-Chain Peptides After Intravenous Bolus Injection in the Rat, Stehle et al., *J. Nutr.* 118:1470-1474 (1988).

Intestinal Disappearance and Portal Blood Appearance of Amino Acids in Sheep, Tagari, et al., *J. Nutr.* 108:790-803 (1978).

Effect of Hydrogen Ion-gradient on Carrier-Mediated Transport of Glycylglycine Across Brush Border Membrane Vesicles from Rabbit Small Intestine, Takuwa et al. *Jap. J. Physiol* 35:629-642 (1985).

Protein and Non-protein Nitrogen for Ruminants, Tamminga et al., U.N. *Economic Comm. for Europe Seminar*, Elmsford, NY pp. 9-31 (1977).

Influx of Glycylsarcosine and L-lysly-L-lysine into Hamster Jejunum In Vitro, Taylor et al., *Clin. Sci.* 58:221-225 (1980).

Nutritional Ecology of the Ruminant, VanDoest, *Comstock Pulishing Associates*, pp. 230-248 (1982).

Amino Acid and Peptide Absorption from the Gastrointestinal Tract, Webb, *Fed. Proc.* 45:2268-2271 (1986).

Intestinal Absorption of Protein Hydrolysis Products: A Review, Webb, *J. Anim. Sci.* 68:3011-3022 (1990).

The Absorption of Peptides, Wiggans et al., *Biochim. Biophys. Acta* 32:69-73 (1959).

Net Metabolism of Plasma Amino Acids by Liver and Portal-Drained Viscera of Fed Sheep, Wolff et al., *Am. J. Physiol.* 223:438-446 (1972).

Comparative Effects of Protein, Protein Hydrolysate and Amino Acid Diets on Nitrogen Metabolism of Normal, Protein-Deficient, Gastrectomized or Hepatectomized Rats, Yamamoto, et al., *J. Nutr.* 115:1436-1446 (1985).

MEAN FLUX OF FREE AMINO ACIDS AND PEPTIDE AMINO ACIDS
ACROSS THE STOMACH OF SHEEP

MEAN FLUX OF FREE AMINO ACIDS AND PEPTIDE AMINO ACIDS
ACROSS THE INTESTINE OF SHEEP

COMPOSITIONS AND METHODS FOR THE TREATMENT OF DIETARY DEFICIENCIES

FIELD OF THE INVENTION

The present invention relates to the treatment of dietary deficiencies of animals, especially ruminants, and relates more particularly to compositions capable of absorption into the blood stream through the stomach and their use in supplying nutrients and treating dietary deficiencies or other maladies.

BACKGROUND OF THE INVENTION

Vast sums of money are spent annually to provide high protein feeds to agricultural animals. The productivity and growth of all animals, including humans but particularly agricultural animals, is dependent upon their ability to ingest sufficient nutrients, such as protein, carbohydrates, and minerals. Synthesis of proteins necessary for high productivity and growth requires that animals absorb sufficient amounts of peptides and amino acids into their blood streams. Of the twenty three amino acids found in the proteins of most animals, only thirteen of these can usually be synthesized in nutritionally adequate amounts by biochemical processes in the body from other substances in the diet. The ten other amino acids which can not be synthesized in sufficient quantities must therefore be ingested by the animal. (Generally, proteins are polymers formed from at least 100 amino acid residues, and peptides are oligomers comprised of from two to ten amino acids joined through amide linkages; dipeptides, tripeptides, and tetrapeptides are formed by condensation of two, three, and four amino acids, respectively.)

Therefore, it is common practice to supplement the diet of animals with nutritional sources containing especially those amino acids which can not be synthesized, or to supplement the diet with sources which can be broken down by the body to form such amino acids; otherwise, the productivity and growth of the animals may be limited in proportion to the amino acid deficiency. Obviously, however, merely increasing the available quantities of the limiting amino acids ingested by an animal does not ensure that the amino acids will ultimately be absorbed and synthesized into protein.

For example, when food is consumed by ruminants, such as sheep and cattle, it enters a complex stomach composed of four compartments, the rumen, the reticulum, the omasum, and the abomasum; the reticulum and the rumen are referred to a the reticulorumen. According to D. C. Church, food entering the reticulorumen is degraded by large populations of bacteria, protozoa, and fungi which reside there. See "Digestive Physiology and Nutrition of Ruminants," Vol. 1, O.S.U. Book Store Inc. of Corvallis, Oreg., herein incorporated by reference. The microbial degradation activity in the reticulorumen is extensive, especially in the case of carbohydrates and proteins. However, Church believed that only certain products of microbial degradation in the reticulorumen, such as volatile fatty acids and ammonia, are actually absorbed from the reticulorumen, while undegraded food residues and microorganisms pass from the reticulorumen to subsequent sections of the gastrointestinal track, where more digestion and absorption occurs.

It has also generally been accepted that dietary protein is either degraded by microorganisms in the reticulorumen, or it is passed through the reticulorumen to subsequent regions of the gastrointestinal track; dietary protein passing from the reticulorumen is then thought to be hydrolyzed to peptides and eventually to amino acids which can be readily absorbed from the intestines of the animal.

Products of dietary protein degradation in the reticulorumen were thought to be essentially utilized by microorganisms to synthesize new proteins for their cellular structures and metabolic functions; this degradation is believed to primarily result in the formation of ammonia, with some peptides and amino acids also being formed for further degradation. Peptides resulting from microbial protein hydrclysis in the reticulorumen were assumed by the prior art to be either utilized by bacteria, or degraded further to ammonia and keto acids.

It has also been widely believed that ammonia is the only nitrogen-containing product of protein degradation absorbed from the stomach. Ammonia utilization in animals is minimal, absorbed ammonia being excreted as urea.

Recent evidence suggests that large quantities of peptides are also formed in the reticulorumen, and that certain peptides are utilized by bacteria residing in the reticulorumen; other peptides formed in the reticulorumen are thought to pass through the omasum and the abomasum into the small intestine where further digestion and/or absorption occurs. The prior art concluded from this that amino acids needed by ruminant animals for protein synthesis were derived from dietary protein which had passed from the reticulorumen without degradation and from microbially generated proteins, all of which were believed to be digested in and absorbed from the small intestine and not from any part of the stomach.

Since the supply of microbially generated protein passing to the intestinal tract is limited by the rate at which microorganisms replicate in the reticulorumen, most efforts for increasing protein uptake by ruminant animals have attempted to increase the amount of undegraded protein reaching the small intestine; generally, this involved feeding animals proteins which are naturally resistant to microbial degradation, or feeding animals proteins which were treated with compounds, such as formaldehyde or tannin, to decrease degradation in the reticulorumen.

Wu et al., in U.S. Pat. No. 4,595,584, herein incorporated by reference, state that the natural nutritional balance of ruminant animals was primarily a function of the microbial composition and population, and that the rate of meat, wool, flesh, or milk production could be increased if sources of growth limiting essential amino acids, and/or medicaments were protected from alteration by microorganisms residing in the rumen; the protected compounds are then thought to become available for direct absorption by the animal later in the gastrointestinal track. Therefore, Wu et al. formed pellets for oral administration which had a core material containing necessary nutrients or medicaments, and the cores were coated, e.g. with an enteric coating, to protect them while in the rumen; the coating was designed to dissolve in the acidic conditions of the abomasum so that the core material could be broken down into a form which the organisms were capable of utilizing.

Despite the widely held belief that amino acid and peptide absorption only occurs further along in the gastrointestinal track than the stomach, it has been ascertained experimentally that certain peptides are not only absorbed into the blood stream through the lining of ruminant stomachs, but some peptides are apparently absorbed more efficiently through the stomach lining. It is believed this absorption is primarily carried out through the lining of the reticulorumen and omasum, rather than the abomasum, because of the large absorptive area in the former compartments. This indicates that prior art attempts to protect protein and medicament containing feeds from degradation in the stomach may actually be counterproductive. Since any peptides in such coated feeds which are capable of being absorbed through the stomach lining are prevented from doing so, feeds protected from microbial degradation may result in reduced utilization of dietary proteins. Further, due to the increased quantity of amino acids in the small intestine resulting from coated feeds, competition for absorption is increased and the efficiency of amino acid absorption may be substantially decreased.

Optimal dietary protein formulations for high producing . ruminants, such as beef cattle and lactating dairy cattle, have not been realized using protected feeds; this is evident from the substantial amounts of waste products from dietary protein excreted in the urine and feces of animals fed prior art feeds, which indicates that optimal mixtures of protein and amino acids are not being presented for digestion and utilization.

It is believed that methionine and lysine are the principle limiting amino acids in ruminant diets, with histidine, phenylalanine, and threonine also playing important limiting roles. Adding these amino acids in synthetic form to ruminant diets has not been effective as the amine acids are destroyed by the microbial population in the reticulorumen, making them unavailable to the animal. Peptides which contain these amino acids and which also resist microbial degradation in the reticulorumen long enough to be absorbed from the stomach, will result in substantial improvements in animal productivity at reduced cost by ensuring that the animals uptake the proper amount of essential amino acids. A further benefit of peptide absorption through the stomach is a reduction in the metabolic energy expenditure required for the absorption of nutrients; since the energy lost in transporting a single amino acid across an absorptive membrane is about the same as transporting a peptide containing multiple amino acid residues, peptide absorption would reduce the energy required to absorb the amino acid needs of the animal. (Absorbed peptides would subsequently be hydrolyzed to their constituent amino acids for use in protein synthesis.)

Thus, there is a need for compositions containing peptides which are capable of absorption from the stomach in order to assure adequate uptake of necessary amino acids. Further, there is a need for methods of treating dietary deficiencies in animals and/or supplying necessary nutrients to animals which does not require coating or other treatment of the nutrients contained therein to prevent microbial degradation or breakdown in the stomach.

While normal or conventional dietary compositions for animals may, and presumably do, contain some amount of peptides, given the conviction of prior workers that such ingested peptides would be degraded in the stomach to nutritionally useless by-products or at the least would not undergo absorption until reaching the intestines, at which point the much larger amount of true protein would release its nutritional components at far more significant levels compared to what might be contributed by the peptides, it is hardly surprising that the possible presence of peptides in the feed was ignored, and not even measured in typical analyses of dietary compositions. Under such circumstances, there was no reason for modifying the normal diet to augment whatever starting amount of peptide might have naturally been present, and even less reason to emphasize the selection of peptides characterized by residues of especially valuable or essential amino acids. Further, there was no incentive to take peculiar advantage of the simple structure of lower oligomeric peptides to synthesize special peptides having enhanced levels of such amino acids. However, in this manner the present invention overcomes specific dietary deficiencies in particular animals on the one hand, while on the other, the diet for normal animals can be tailored to optimize the function of the animal in producing meat, milk, offspring, etc. cl SUMMARY OF THE INVENTION Once the fundamental phenomena of the invention are comprehended, the formulation of suitable feed compositions will be immediately obvious to those knowledgeable in the field so that detailed discussion becomes unnecessary; suitable compositions contain peptides, or peptide derivatives, or peptide precursors that release peptides within the stomach by gastric action, the peptides being capable of absorption into the blood stream through the lining of the stomach of animals ingesting them to supply particular nutrients to ruminants and other animals. In a preferred embodiment, feed compositions are modified to incorporate significant amounts of peptides containing one or more amino acid residues in which an animal is deficient. In formulating preferred feed compositions, the peptides selected are those which have been determined to be absorbed in substantial amounts through the lining of the stomach. Synthetic peptides may be used, or feed stocks containing proteins and polypeptides which break down to form peptides which can be absorbed through the stomach lining may be used.

As an alternative embodiment, the possibility exists for complexing peptides capable of absorption into the blood stream through the stomach lining with medicaments or mineral containing compounds which an animal requires, and feed compositions containing these peptide derivatives are fed to nutrient-deficient animals or animals suffering from an illness for which the medicament is effective. In another specific embodiment, compositions are formulated to incorporate peptides or peptide derivatives that contain proline, phenylalanine, or glycine, that appear to be preferentially absorbed in the stomach as well at least one other less readily absorbable amino acid or nutrient in which an animal is deficient in order to facilitate the absorption of the latter into the blood stream through the lining of the stomach.

In a preferred process for providing nutrients to ruminants, or for treating dietary deficiencies in ruminants, feed compositions are formulated which contain increased amounts of peptides known to be absorbed into the blood stream through the lining of the stomach. Preferred peptides contain proline, glycine, or phenylalanine, and have no more than two to four amino acid residues; preferably, the peptides are supplied to animals in concentrations greater than can be found in any conventional feed source. Natural sources containing sufficient concentrations of desired peptides which can be absorbed through the stomach may also be used in a preferred method of supplying nutrients and treating dietary deficiencies.

Thus, it is a primary object of the present invention to provide feed compositions which contain peptides that are capable of absorption into the blood stream through the lining of the stomach.

It is a further object of the present invention to provide feed compositions for ruminants which contain peptides that resist microbial degradation in the reticulorumen and which are absorbed into the blood stream from the stomach.

It is yet another object of the present invention to provide a method for the treatment of dietary deficiencies which involves modifying the dietary intake of animals to incorporate increased levels of peptides or peptide derivatives providing essential nutrients for absorption in the stomach of such animals and into the blood stream thereof.

DETAILED DESCRIPTION OF THE INVENTION

It has been discovered that peptides, particularly oligomeric peptides containing two to about four amino acid residues, can be absorbed from the stomach region of ruminants, such as beef cattle, dairy cattle, and sheep, into the blood stream of the animals. This knowledge can be applied to increase the uptake of specific nutrients by manipulating the diet of animals, such as but not limited to ruminants, to incorporate high level of selected peptides containing specific amino acid residues capable of achieving more efficient animal growth and production.

ABSORPTION OF PEPTIDES THROUGH THE RETICULORUMEN OF RUMINANTS

Studies of ruminants were undertaken to determine uptake of peptides and amino acids through the lining of the stomach. From these studies came the discovery that peptides, preferably peptides containing four amino acids or less, are absorbed through the lining of the stomach, which is contrary to the widely held belief that digestion products of proteins are only absorbed from the intestinal region of the gastrointestinal track of ruminants and other animals.

Figure 1:
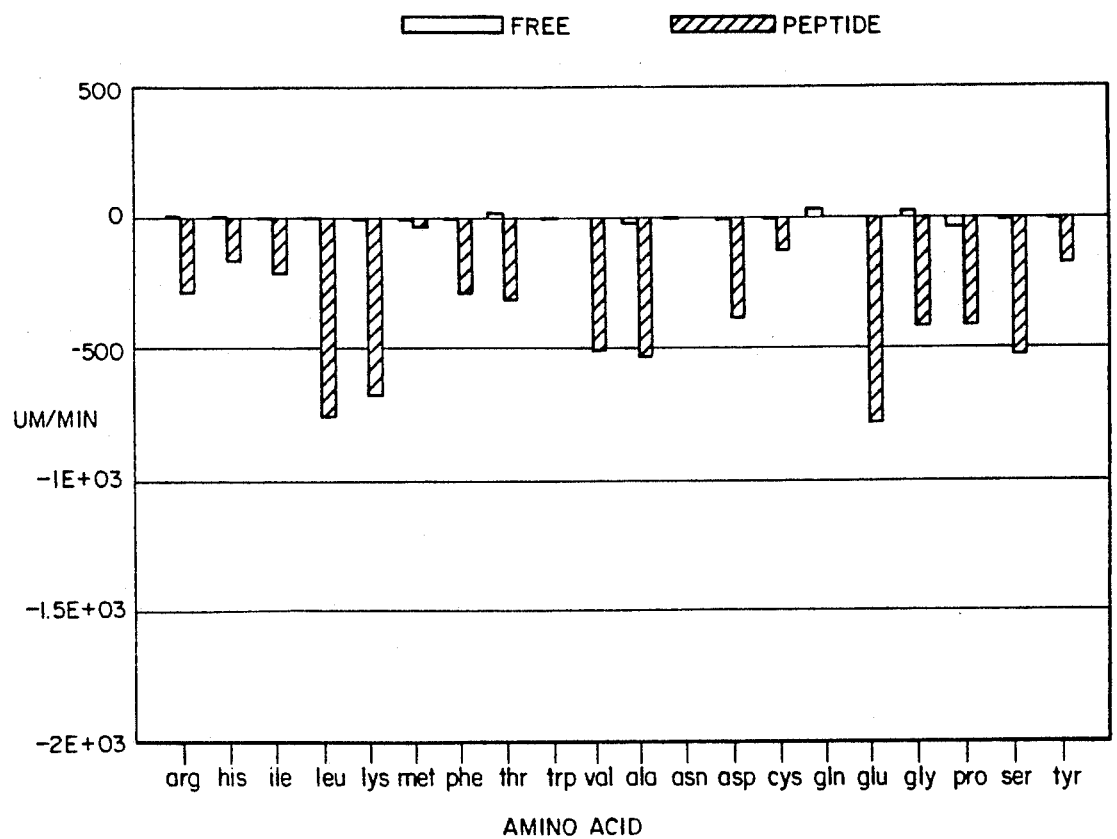
FIG. 1 is a chart of the mean flux in micromoles per minute (UM/MIN) of free amino acids and peptide amino acids across the stomach of sheep.

The discovery of this phenomenon was based upon measurements of the free amino acid and peptide amino acid flux across the stomachs of sheep and cattle. By "free amino acid" is meant those amino acids absorbed directly into the blood stream, while "peptide amino acid" refers to amino acids recovered from peptides absorbed into the blood stream, and subsequently hydrolyzed to their constituent amino acids. With reference to FIG. 1, the mean fluxes in micromoles per minute (UM/MIN) of free amino acids and peptide amino acids across the stomach of sheep are presented. All of the sheep studied were fed the composition having the ingredients listed below in Table 1.

TABLE 1

| SHEEP FEED COMPOSITION INGREDIENTS[a] | |
|---|---|
| INGREDIENT | WEIGHT PERCENT[b] |
| Corn, ground | 50.00 |
| Orchardgrass Hay | 30.00 |
| Soybean Meal | 13.30 |
| Molasses | 5.00 |
| Defluorinated Rock Phosphate | 0.42 |
| Limestone | 0.78 |
| Trace Mineralized Salt | 0.50 |
| Dry Matter | 91.06 |
| Crude Protein[c] | 13.92 |

[a]All animals received intramuscular injections of vitamin A, 500,00 IU; vitamin D, 75,000 IU; vitamin E, 3.7 IU/kg body weight; and selenium, 55 µg/kg body weight.
[b]As fed basis.
[c]Dry matter basis.

Peptide and amino acid fluxes across the stomach lining were calculated as the products of blood flows through the tissue and the arteriovenous changes in the concentrations of the nutrients. The negative values in FIG. 1 represent an output of the nutrients into the venous blood draining the tissue, and indicate absorption. Note that free amino acids do not appear to be absorbed to any significant degree through the stomach, but surprisingly large amounts of peptide amino acids are absorbed through the stomach into blood draining the stomach region.

In order to determine the amounts of peptides and amino acids absorbed respectively from the stomach and the intestines, the peptide and amino acid content of arterial blood plasma was compared to the peptide and amino acid content of venous blood plasma; venous blood from the portal vein (which drains both stomach and intestinal regions of the gastrointestinal track) and blood from the mesenteric vein (which drains only the intestinal region) were collected, and analyzed. Differences in the composition of the portal vein blood plasma and the mesenteric vein blood plasma reflect the composition of blood plasma draining the stomach region.

Amino acids analyzed for were alanine (ala), arginine (arg), asparagine (asn), aspartic acid (asp), cysteine (cys), glutamic acid (glu), glutamine (gln), glycine (gly), histidine (his), isoleucine (ile), leucine (leu), lysine (lys), methionine (met), phenylalanine (phe), proline (pro), serine (ser), threonine (thr), tryptophan (trp), tyrosine (tyr), and valine (val).

Blood samples to be analyzed were first treated to remove protein and large polypeptides from the blood plasma by passing the plasma through filters which excluded molecules having a molecular weight greater than ten thousand daltons; this molecular weight cut off point was chosen because earlier work showed that most of the peptides in the blood plasma of calves had molecular weights of five hundred daltons or less. Aliquots of the filtrates were then analyzed for their free amino acid content. Additional aliquots of the filtrates were treated with HCl to hydrolyze the peptide bonds, and the hydrolyzed solutions were analyzed for their total amino acid content. The difference between the total amino acid content and the free amino acid content yielded the peptide amino acid content of the blood plasma (although this did not provide sufficient information to determine the composition of specific peptides in the plasma).

Figure 2:
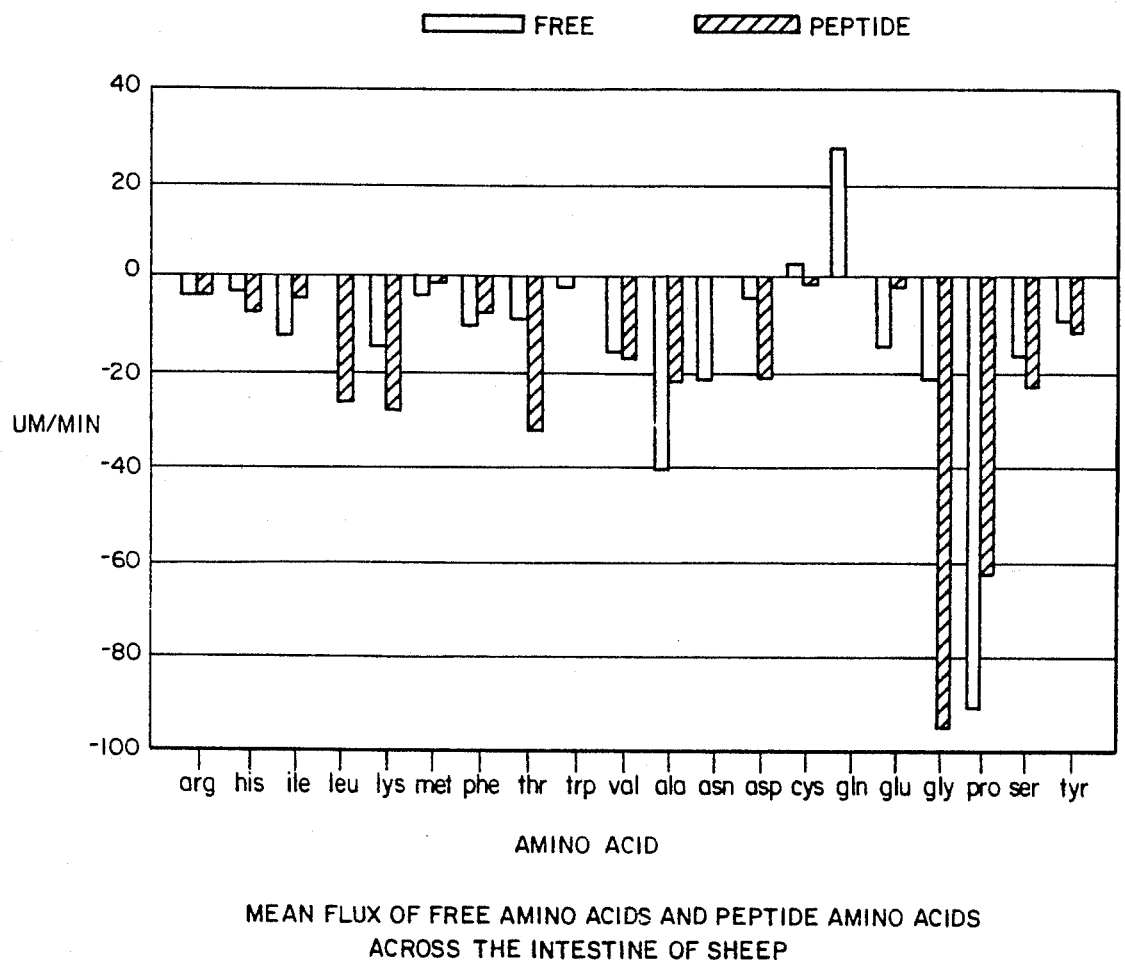
FIG. 2 is a chart of the mean flux in micromoles per minute (UM/MIN) of free amino acids and peptide amino acids across the intestines of sheep.

Observations were made of free amino acids and peptide amino acids in venous blood draining the intestinal region. These observations also enable testing of the current wide spread belief that amino acids (i.e. free amino acids) are absorbed from the small intestine, but not from the stomach. With reference to FIG. 2, the mean flux in micromoles per minute (UM/MIN) of free amino acids and peptide amino acids across the intestines of sheep are presented on a considerably enlarged scale in comparison to FIG. 1. Note that both free amino acids and peptide amino acids were observed in the blood plasma draining the intestine, but minimal absorption of free amino acids were observed across the lining of the stomach.

Since FIG. 1 shows little absorption of free amino acids through the stomach, while FIG. 2 demonstrates substantial absorption of amino acids in the intestine, the prior art theory of virtually exclusive intestinal amino acid absorption appears to be confirmed. A comparison of the mean fluxes of peptide amino acids across the stomach of sheep versus the mean fluxes of peptide amino acids across the intestines demonstrates that the amount of peptides absorbed through the lining of the stomach is several times the amount of peptides that are absorbed from the intestine.

A preferred method for determining the identity and amounts of peptide amino acids absorbed through the stomach involves a six step process (although there is no requirement that the steps be performed in any given order). In the first step, the concentration of free amino acids in a portal vein blood plasma sample is subtracted from the concentration of amino acids in a portal vein blood plasma sample which has been treated to hydrolyze peptides contained therein. This provides the portal vein peptide concentration.

In the second step, the mesenteric vein peptide concentration is determined by subtracting the free amino acid concentration in a mesenteric vein blood plasma sample from the amino acid concentration in a hydrolyzed mesenteric vein blood plasma sample.

The third step involves determination of the arterial peptide concentration by subtracting the free amino acid concentration in an arterial blood plasma sample from the total amino acid concentration in an arterial blood plasma sample which has been hydrolyzed.

Step four involves subtracting the arterial peptide concentration from the mesenteric peptide concentration to obtain the intestinal peptide concentration. The flux of peptides across the intestinal lining can then be determined by multiplying the intestinal peptide concentration by blood flow.

In a fifth step, arterial peptide concentration is subtracted from the portal vein peptide concentration to yield the total peptide concentration. The total peptide flux from the entire gastrointestinal system is then determined by multiplying the total peptide concentration by the blood flow.

The intestinal peptide flux is then subtracted from the total peptide flux in a sixth step to obtain the stomach peptide flux.

Using the above method, it is possible to determine the amounts of peptide amino acids absorbed through the stomach independently of the amounts absorbed through the intestines. Although the method does not provide the identity of specific peptides absorbed, one of skill in the art can determine the absorption of particular peptides by providing only one peptide or several peptides and/or proteins at a time and monitoring absorption; other analytical techniques may also be used to determine specific peptide uptake.

FORMULATION OF PREFERRED COMPOSITIONS

It is also known that the bonds between certain amino acids are more resistant to enzymatic hydrolysis than others. For example, the bonds between glycine, proline, or phenylalanine with other amino acids appear more resistant to hydrolysis in the reticulorumen than other peptide bonds, thereby favoring absorption of peptides containing residues of such amino acids in the stomach. Thus, in a preferred embodiment, proline, glycine, or phenylalanine are attached to amino acids which an animal requires for a healthy diet, or which an animal is deficient in and the peptides are fed directly or are incorporated into a feed composition. It is believed that the preferred peptides are more likely to survive the microbial environment of the reticulorumen, although other peptides which do not contain glycine, phenylalanine, or proline will also be effective, provided sufficient amounts are fed to compensate for any degradation in the stomach.

Preliminary studies indicate that peptides formed of between two and four amino acid residues are absorbed to a greater extent through the stomach of ruminants than peptides containing greater amounts of amino acid residues. Thus, it is preferred that the peptides and peptide derivatives used to supply nutrients, treat dietary deficiencies, or provide medicaments to the blood stream of animals by absorption through the stomach will contain between two and four amino acid residues.

It is also envisioned that proteins can be included in the diet which degrade in gastric conditions to form peptides that can be absorbed through the lining of the stomach, and hence act as precursors for the desired peptides. Thus, the present invention also extends not only to feed compositions containing natural or synthetic sources of peptides which can be absorbed through the stomach, but also to feed compositions containing natural or synthetic sources of proteins or peptides which degrade in the stomach to release those peptides which can be absorbed through the stomach.

In an alternative embodiment, peptide derivatives can be formed by binding chelated minerals, antibiotics, or medicaments to peptides; it is envisioned that these peptide derivatives will also be capable of absorption through the lining of the stomach for providing nutrients, or treating dietary deficiencies or illnesses.

Another embodiment of the present invention includes selective fermentation of proteins with particular microorganisms to produce specific peptides. Alternatively, one may use naturally occurring or genetically engineered bacteria to produce specific peptides. Such bacteria or their products could be harvested and incorporated into the diet of animals to overcome dietary deficiencies.

While it will be apparent from the foregoing to one of skill in the art how to perform the present invention, the following non-limiting example is provided to facilitate understanding and utilizing the compositions and methods disclosed above for supplying nutrients, and treating dietary deficiencies and disease by absorption of peptides and peptide derivatives through the stomach.

EXAMPLE 1

Methionine deficiencies are frequently encountered with ruminant animals. Since peptides formed of methionine bound to proline, glycine, or phenylalanine are expected to be more likely to resist microbial enzymatic hydrolysis in the reticulorumen than other peptides, these peptides can be synthesized, and fed directly to a ruminant animal, or proteins which are degradable in the reticulorumen to produce peptides containing methionine can be fed to a methionine deficient animal. Preferably, prolylmethionine (or methionylproline), or a methionine-containing peptide having no more than two to four amino acid residues, is incorporated into the diet of a ruminant animal suffering from a methionine deficiency.

In a similar fashion, arginine, histidine, threonine, tryptophan, isoleucine, leucine, valine, lysine, or other amino acid deficiencies can be treated by adding peptides containing . these amino acids to the diet. Preferably, the peptides containing these amino acids will contain no more than two to four amino acid residues, and will preferably also contain glycine, phenylalanine, or proline.

In these inventions, peptides can and will be incorporated in the diet at concentrations greater than found in any natural source. In an alternative embodiment, preferred compositions contain peptides which are capable of absorption through the stomach, and which contain relative quantities of amino acids/amino acid residues which promote the most efficient and effective protein synthesis possible. It is envisioned that any naturally occurring nutrient sources containing peptides, or containing compounds which can be degraded to form peptides, in which the peptides are capable of absorption by the stomach and contain important amino acids, might be used to perform the present invention, with their relative proportions in the diet being adjusted upward as necessary to insure an enhanced concentration of the selected peptides in the diet.

Thus, the present invention discloses new compositions and methods for providing nutrients, and treating dietary deficiencies and illnesses in animals, such as but not limited to ruminants. From the above teachings, it is apparent that many modifications and variations of the present pioneer invention are possible. It is therefore to be understood that the invention may be practiced otherwise than as it is specifically described.

We claim:

1. In a feed composition for providing nutrients to ruminants, said composition comprising:
   an effective amount of peptides sufficient to increase the amino acid concentration available for metabolic utilization in ruminants when a sufficient quantity of said composition is ingested by ruminants, said peptides being capable of absorption into the blood stream through the liming of the reticulorumen and omasum of a ruminant ingesting said composition;
   said peptides having the formula AB, wherein A is the N terminal amino acid residue and is selected from the group comprised of proline and phenylalanine; and
   B comprises from one to three amino acid residues, said residues being the same or different and selected from the group comprised of alanine, glycine, methionine, arginine, threonine, tryptophan, histidine, isoleucine, leucine, lysine, asparagine, aspartic acid, glutamic acid, glutamine, serine, tyrosine, and valine.

2. A composition according to claim 1, wherein A is selected from the group comprised of proline, phenylalanine, methionine, threonine, tryptophan, histidine, isoleucine, leucine, asparagine, aspartic acid, glutamic acid, glutamine, serine, tyrosine, and valine; and
   B comprises proline, phenylalanine and glycine.

3. A composition according to claim 1 wherein A is proline and B is methionine.

4. A method for the treatment of amino acid deficiencies in ruminants comprising the step of:
   feeding an effective amount of a composition to a ruminant suffering from a deficiency of at least one amino acid, said composition comprising at least one peptide, said at least one peptide comprising at least one amino acid residue of an amino acid which said ruminant is deficient in, wherein said at least one peptide is capable of absorption into the blood stream of said ruminant through the reticulorumen and omasum, wherein the concentration of said amino acid in the blood is increased.

5. A method according to claim 4, wherein:
   said peptide further comprises at least one amino acid residue formed from an amino acid selected from the group comprised of proline, phenylalanine, and glycine, and said peptide comprises between two and four amino acid residues.

6. A method according to claim 5, wherein:
   said peptide further comprises at least one amino acid residue formed from an amino acid selected from the group comprised of: methionine, arginine, threonine, tryptophan, histidine, isoleucine, leucine, lysine, and valine.

7. A method according to claim 4, further comprising the step of:
   producing said peptides by fermenting proteins with microorganisms.

8. A method according to claim 4, further comprising the steps of:
   producing said peptides by growing bacteria which produce said peptides, said bacteria being selected from the group comprised of naturally occurring bacteria and genetically engineered bacteria, harvesting said bacteria, and incorporating into said composition said bacteria, or the products of said bacteria.

9. A method according to claim 4 wherein said composition comprises an effective amount of a peptide comprising residues of proline and methionine.

10. A method of modifying the dietary intake of a ruminant to increase the level absorbed by said ruminant of at least one selected amino acid essential to the dietary requirements of said ruminant which comprises the step of:
    incorporating into the dietary intake of said ruminant at least one peptide or a synthetic precursor of said at least one peptide which is capable of absorbtion through the reticulorumen and omasum of said ruminant, said at least one peptide or precursor being present in an amount sufficient to increase the absorbed level of said at least one amino acid above that achieved by the normal dietary intake of said ruminant.

11. A method for the treatment of amino acid deficiencies in ruminants comprising the step of:
    feeding an effective amount of a composition to a ruminant suffering from a deficiency of at least one amino acid, said composition being capable of making available at least one peptide in the reticulorumen and omasum of a ruminant, said at least one peptide comprising at least one amino acid residue of an amino acid which said ruminant is deficient in, wherein said at least one peptide is capable of absorption into the bloodstream of said ruminant through the reticulorumen and omasum wherein the concentration of said amino acid in the blood is increased.

12. The method of claim 11, wherein:

said at least one peptide has the formula AB, wherein

A is the N terminal amino acid residue and is selected from the group comprised of proline and phenylalanine; and B comprises from one to three amino acid residues, said residues being the same or different and selected from the group comprised of alanine, glycine, methionine, arginine, threonine, tryptophan, histidine, isoleucine, leucine, lysine, asparagine, aspartic acid, glutamic acid, glutamine, serine, tyrosine, and valine.

* * * * *